United States Patent
Lin

(10) Patent No.: US 8,700,348 B2
(45) Date of Patent: Apr. 15, 2014

(54) CONTACT-TYPE OBJECT WATER CONTENT SENSING DEVICE AND METHOD AND COMPUTER PROGRAM PRODUCT

(75) Inventor: Chien-Der Lin, Kaohsiung (TW)

(73) Assignee: Institute for Information Industry, Taipei (TW)

( * ) Notice: Subject to any disclaimer, the term of this patent is extended or adjusted under 35 U.S.C. 154(b) by 695 days.

(21) Appl. No.: 12/970,658

(22) Filed: Dec. 16, 2010

(65) Prior Publication Data

US 2012/0136597 A1    May 31, 2012

(30) Foreign Application Priority Data

Nov. 26, 2010 (TW) .............................. 99141009 A

(51) Int. Cl.
*G01R 25/00* (2006.01)
(52) U.S. Cl.
USPC .......................................................... 702/65
(58) Field of Classification Search
USPC .......................................................... 702/65
See application file for complete search history.

(56) References Cited

U.S. PATENT DOCUMENTS 6,474,156 B1 * 11/2002 Endo et al. .................. 73/290 V

FOREIGN PATENT DOCUMENTS

CN         1330268 A       1/2002

* cited by examiner

*Primary Examiner* — Tung S Lau
*Assistant Examiner* — Xiuquin Sun
(74) *Attorney, Agent, or Firm* — Muncy, Geissler, Olds & Lowe, P.C.

(57) ABSTRACT

A contact-type object water content sensing device and method and a computer program product are presented. The device includes a power unit, a sensing unit, and an calculating unit. The sensing unit includes a substrate and a copper foil, and the copper foil is configured on the substrate. The sensing unit is used to contact a target object and a power unit is used to supply power to the copper foil. The copper foil when supplied with power forms an equivalent capacitor, and the equivalent capacitor has different capacitances in correspondence to a water content of the target object. The calculating unit is electrically connected to the sensing unit and is used to analyze the capacitance of the equivalent capacitor, so as to calculate the water content of the target object.

7 Claims, 7 Drawing Sheets

CONTACT-TYPE OBJECT WATER CONTENT SENSING DEVICE AND METHOD AND COMPUTER PROGRAM PRODUCT

CROSS-REFERENCE TO RELATED APPLICATION

This application claims the benefit of Taiwan Patent Application No. 099141009, filed on Nov. 26, 2010, which is hereby incorporated by reference for all purposes as if fully set forth herein.

BACKGROUND OF THE INVENTION

1. Field of Invention

The present invention relates to an object water content sensing device and method, and more particularly to a sensing device and method for sensing a water content of an object by contacting the object and a computer program product.

2. Related Art

Contact-type water content sensors in the prior arts have the following types. (1) A sensing element is formed by etching a circuit on an insulating substrate and configuring a chemical substance, for example, a polymer material, on the substrate surface, so as to present a water content of the environment where the sensing element is located through the chemical changes of the chemical substance. (2) A sensing element is fabricated by a ceramic material together with a circuit design, that is, a porous water absorption characteristic of the ceramic in combination with an electric conductivity regulation technique, thereby deducing the water content of the environment where the sensing element is located through the electricity conductivity change of the substance caused by water absorption. (3) The sensing element is combined with an ionic conduction technique of an electrolyte solution, and the water absorption of the sensing element affects a variation of the ionic conductivity of the electrolyte solution, thereby deducing the water content of the environment where the sensing element is located through the variation. (4) The sensing element is combined with a heat transfer technology, and based on the characteristic that water absorbs heat, the variation of the thermal conductivity of the substance caused by the water absorption is utilized to deduce the water content of the environment where the sensing element is located.

However, the sensing element with the chemical substance configured on the surface is formed by combining two electrical pole pieces with the chemical substance, and combining the electrical pole pieces and the chemical substance with the circuit of the insulating substrate to form one piece, which has a rather complicated working process. Likewise, the sensing element adopting the electrolyte solution technique needs preparing the proper electrolyte solution to combine with the sensing element and meanwhile needs analyzing the ionic conductivity of the electrolyte solution, so the fabricating complexity of the sensing element is not low and the cost is high. Secondly, the contact-type water content sensor with chemical substances configured on the surface needs sensing the water content of the target object for example, a soil water content and a powder water content, in a contact manner. However, undesired chemical reactions of these chemical substances may occur due to the long-time contact with the target object, which induces the deterioration of the chemical substances (denaturalization, tendering, pulverization, and so on of the chemical substances). Also, the sensing element of the ceramic material contacts the target object for a long time for sensing the water content of the target object all day long, so ceramic parts of the element easily deteriorates, for example, becomes tender or pulverizes, which reduces the life cycle of the element, and the stability of the element is unsatisfied when sensing the water content. Thirdly, the contact-type sensor when applied in sensing the soil water content has the defects of low element life cycle and deterioration of the element, which causes that the contact-type sensor is difficult to be applied in sensing the soil water content for a long time. Moreover, once the element deteriorates, the measured water content data is abnormal and cannot be used, so the soil water content cannot be accurately measured. Fourthly, the target object like soil has complicated liquid components and the liquid components contain water, but the current water content sensors disregard the impure water components, so the measured water content is questionable.

Therefore, it is a subject needing consideration to provide a water content sensor which is not easy to deteriorate and can be used for monitoring the water content of a target object for a long time.

SUMMARY OF THE INVENTION

The present invention is directed to an object water content sensing device and method and a computer program product applicable to contact sensing a water content of a target object.

To solve the above problems of the device, the present invention provides a contact-type object water content sensing device, which comprises a power unit, a sensing unit, and an calculating unit. The sensing unit comprises a substrate and a copper foil, and the copper foil is configured on the substrate. The sensing unit is used to contact a target object, the copper foil when supplied with power form an equivalent capacitor, and the equivalent capacitor has different capacitances in correspondence to the water content of the target object. The power unit is electrically connected to and supplies power to the copper foil. The calculating unit is electrically connected to the sensing unit and is used to analyze the capacitance of the equivalent capacitor, so as to calculate the water content of the target object.

To solve the above problems of the method, the present invention provides a contact-type object water content sensing method, which comprises the following steps. A sensing unit contacts a target object, in which the sensing unit is equipped with a copper foil. A power unit supplies power to the copper foil, the copper foil when supplied with power forms an equivalent capacitor, and the equivalent capacitor has different capacitances in correspondence to different water contents of the target object. An calculating unit analyzes the capacitance of the equivalent capacitor, so as to calculate the water content of the target object.

The present invention further provides a computer program product, which is configured in an calculating unit. The calculating unit is connected to a sensing unit equipped with a copper foil, the sensing unit contacts a target object, and the calculating unit reads the computer program product to execute a contact-type object water content sensing method. The flow is illustrated as above and will not be repeated herein. The present invention may also be implemented as a computer program, and stored in a computer readable recording medium, so that a computer reads the recording medium and then executes the contact-type object water content sensing method. When the computer program is loaded by a computer, a machine, or an electronic device and executed, the computer, machine, or electronic device becomes the device for implementing the present invention.

The present invention is characterized in that, the copper foil is adopted as one of the components of the sensing unit, and the copper foil material may generate obvious physical quantity variation, for example, variation of impedance and capacitance mentioned in the present invention, due to different water contents of the object and the environment in contact and the physical quantity variation has a specific rule, so the copper foil material is beneficial to improving the accuracy in measuring the object water content. Then, due to the metal property of the copper foil, the copper foil will not have the deterioration like ceramic material and polymer material, which not only is beneficial to improving the accuracy in measuring the object water content, but also extends the life cycle of the sensing element and greatly improves the applicability of the sensing device. Thirdly, due to the capacitance variation characteristic of the copper foil, even if the sensing element is applied in sensing the target object having complicated components like the soil, the water content of the impure water liquid may also be measured, so the measured water content is quite accurate.

BRIEF DESCRIPTION OF THE DRAWINGS

The present invention will become more fully understood from the detailed description given herein below for illustration only, and thus are not limitative of the present invention, and wherein.

DETAILED DESCRIPTION OF THE INVENTION

Hereinafter, the details of the embodiments of the present invention will be illustrated with reference to the drawings.

Figure 1:
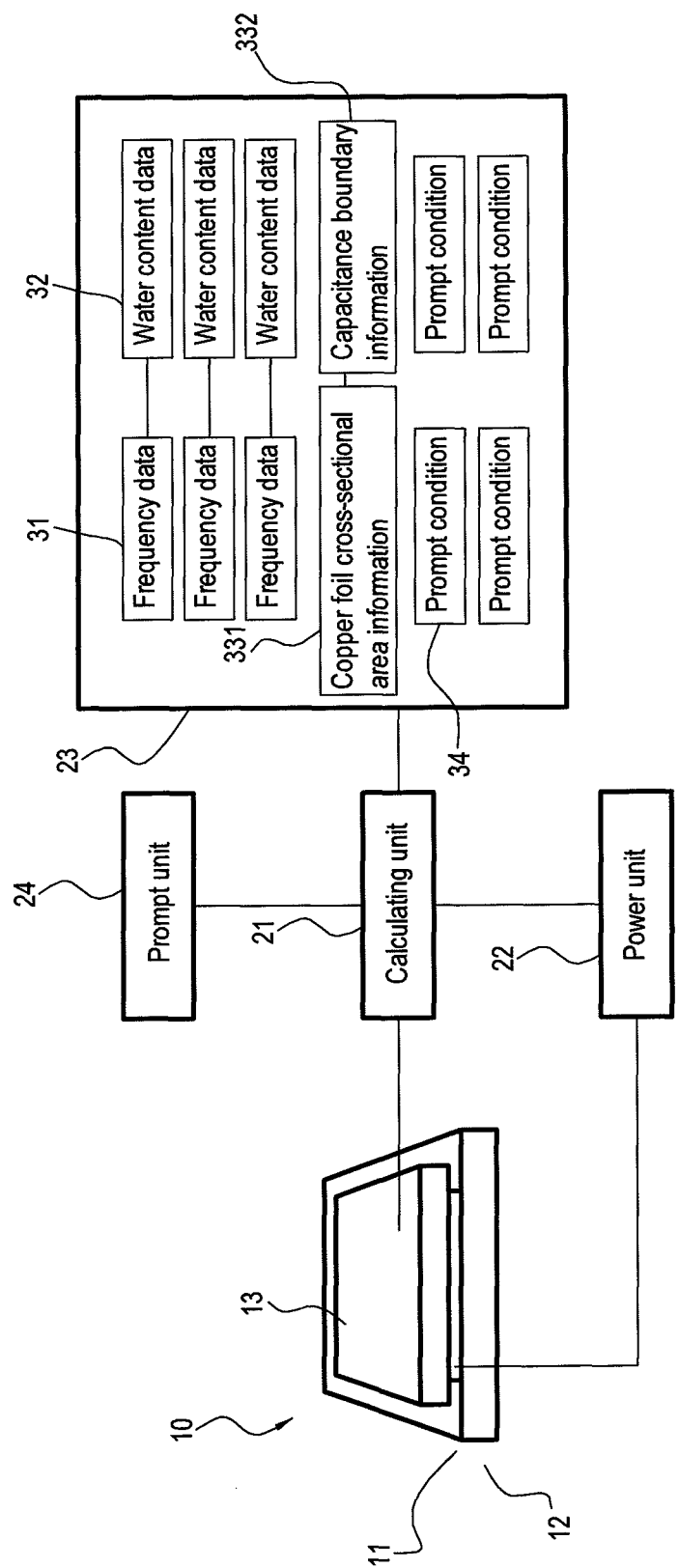
FIG. 1 is a schematic architectural view of a contact-type object water content sensing device according to an embodiment of the present invention.

FIG. 1 is a schematic architectural view of a contact-type object water content sensing device according to an embodiment of the present invention. Referring to FIG. 1, the device mainly includes a sensing unit 10, an calculating unit 21, and a power unit 22.

The sensing unit 10 is equipped with a substrate 11 and a copper foil 12, and the copper foil 12 is configured on the substrate 11. In the following embodiments, the square copper foil 12 is taken as an example for illustration; however, the shape is not limited to square, and the copper foil 12 in the shape of circle, triangle, polygon, or other shapes is also applicable. The sensing unit 10 is used to contact a target object (not shown), and the target object is, for example, the soil, wall, electrical appliance, or an object that can be contacted. In some embodiments of the present invention, the sensing unit 10 may be further equipped with a protection layer 13, and the protection layer 13 is configured on the surface of the copper foil 12. The protection layer 13 is a layer of adhesive film or chemical film, and is used to prevent the oxidation of the copper foil to avoid the influence on the sensing accuracy caused by the oxidation of the copper foil.

The calculating unit 21 and the power unit 22 are respectively connected to the sensing unit 10. The power unit 22 is used to supply power to the copper foil 12, and the copper foil 12 when supplied with power and abutting the target object may form an equivalent capacitor to take a charging/discharging action. In correspondence to different water contents of the target object, the capacitance of the equivalent capacitor differs. The power supply of the power unit 22 may be controlled by the calculating unit 21 or operates independently, depending on the demands of the designer.

Figure 2:
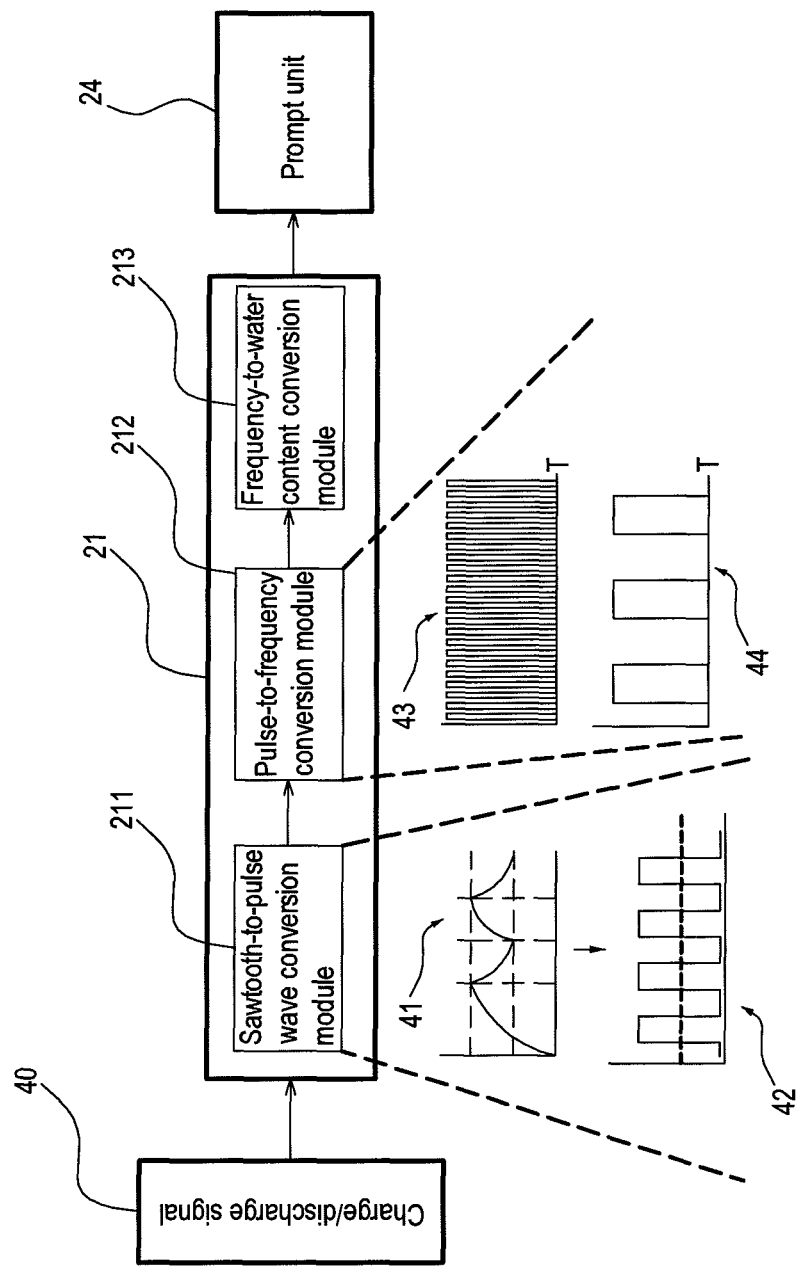
FIG. 2 is a schematic view of signal variations according to an embodiment of the present invention.

In some embodiments, the calculating unit 21 is used to analyze the capacitance of the equivalent capacitor, so as to calculate the water content of the target object. The calculating unit 21 analyzes the water content of the target object. FIG. 2 is a schematic view of signal variations according to an embodiment of the present invention. Referring to FIG. 2, in this embodiment, the copper foil 12 receives the power supplied by the power unit 22 to generate a capacitance, and in correspondence to different water contents of the target object, the capacitance differs, that is to say, the value of the water content of the target object influences the capacitance, and different capacitances influence the charging/discharging time constant, so the corresponding charge/discharge signals are different. The charge/discharge signal is a time accumulated signal, the waveform is a sawtooth wave, and the frequency differs in correspondence to different capacitances, so the frequency may be utilized to calculate the water content.

In other embodiments, the sensing device may further include a memory unit 23 (as shown in FIG. 1), and the memory unit 23 stores a plurality of frequency data 31 and a plurality of water content data 32 corresponding to the frequency data 31. The calculating unit 21 analyzes the capacitance of the equivalent capacitor through the sensing unit 10.

In other embodiments, furthermore, the calculating unit 21 may analyze a charge/discharge signal 40 of the equivalent capacitor, convert the charge/discharge signal into a pulse signal, then convert the pulse signal into a frequency signal, and compare the frequency data by use of the frequency signal, so as to calculate the water content of the target object according to the water content data. The detailed structure of the calculating unit 21 is shown in FIG. 2. The calculating unit 21 includes three signal conversion modules, that is, a sawtooth-to-pulse wave conversion module 211, a pulse-to-frequency conversion module 212, and a frequency-to-water content conversion module 213. When the charge/discharge signal 40 is converted into a timing diagram, a sawtooth wave 41 is presented. The sawtooth-to-pulse wave conversion module 211 regulates the charge/discharge signal 40 to convert the sawtooth wave 41 into a pulse signal 42. Then, the pulse-to-frequency conversion module 212 calculates the frequency of the charge/discharge signal 40 according to the pulse signal 42, so as to convert the above pulse into a corresponding frequency signal. However, according to different signal contents of the pulse signal 42, the converted frequency signals, for example, a high-frequency signal 43 and a low-frequency signal 44 shown in FIG. 2, differ. Thereafter, the frequency-to-water content conversion module 213 compares the frequency data 31 by use of the frequency signal to find out water content data 32 corresponding to the frequency signal, so as to calculate the water content of the target object.

However, the operational data in converting the frequency into the corresponding water content may be stored in the calculating unit 21 or designed in the program executed by the calculating unit 21 in advance, and is not limited to the pre-stored water content data 32 and frequency data 31.

In other embodiments, furthermore, the memory unit 23 further stores copper foil cross-sectional area information 331 and capacitance boundary information 332 corresponding to the copper foil cross-sectional area information 331 (see FIG. 1). The calculating unit 21 firstly acquires the area of the copper foil 12, in which the area is pre-stored in the memory unit 23 or input by the user through an interface of the calculating unit 21 for the calculating unit 21 to use. Then, the calculating unit 21, when analyzing the above capacitance of the equivalent capacitor meets the capacitance boundary information 332 according to the capacitance boundary information 332, starts calculating the water content of the target object.

Figure 3:
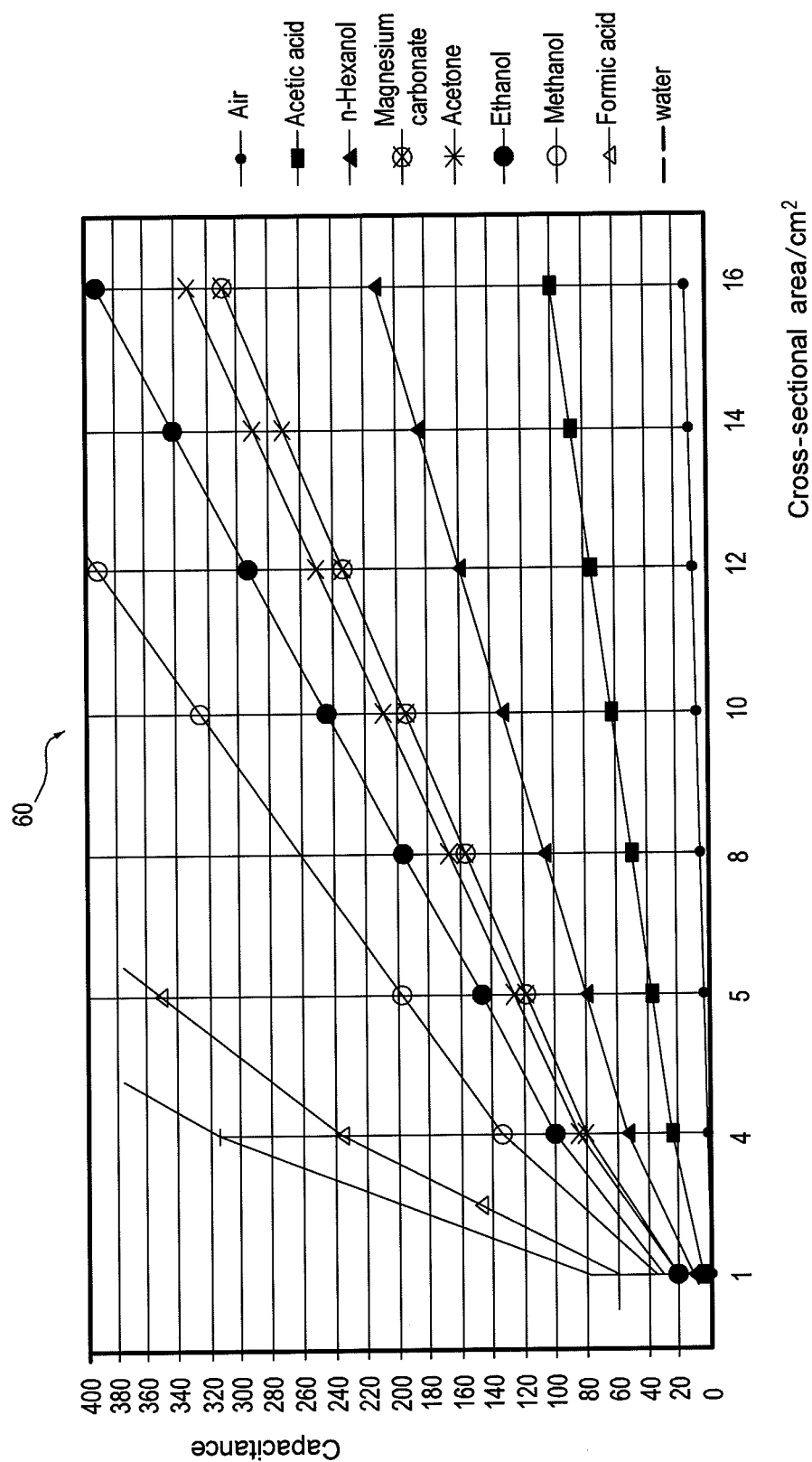
FIG. 3 is a schematic view of an example of a comparison table of a copper foil area and a capacitance according to an embodiment of the present invention.

In other embodiments, furthermore, the capacitance may be calculated according to the area of the area of the copper foil 12. FIG. 3 is a schematic view of an example of a comparison table of a copper foil area and a capacitance according to an embodiment of the present invention. Referring to FIG. 3 together, the capacitance of the equivalent capacitor formed by the copper foil 12 may be obtained by the following Formula 1:

$$C = \frac{\varepsilon_0 A}{d} \quad \text{(Formula 1)}$$

where C=capacitance, $\varepsilon_0$=dielectric constant of the liquid contained in the target object, A=surface area of the copper foil 12 (upper surface area or lower surface area, upper surface area=lower surface area, also the cross-sectional area of the equivalent capacitor), and d=height of the copper foil 12 (i.e., the pitch of the capacitor).

Here, the target object is, for example, soil, and the common components contained in the soil and the dielectric constants include $H_2O$ (water, 78.5), HCOOH (formic acid, 58.5), $HCON(CH_3)_2$ (N, N-dimethyl formamide, 36.7), $CH_3OH$ (methanol, 32.7), $C_2H_5OH$ (ethanol, 24.5), $CH_3COOH_3$ (acetone, 20.7), $n-C_6H_{13}OH$ (n-hexanol, 13.3), $CH_3COOH$ (acetic acid or ethanoic acid, 6.15), $C_6H_6$ (benzene, 2.28), $CCl_4$ (carbon tetrachloride, 2.24), and $n-C_6H_{14}$ (n-hexane, 1.88).

The dielectric constants and the area of the copper foil 12 are combined to be introduced into Formula 1, and then a comparison table 60 of the copper foil area and the capacitance of FIG. 3 is obtained. From Formula 1, when the surface area of the copper foil 12 increases (that is, the cross-sectional area of the equivalent capacitor is increased), the capacitance of the equivalent capacitor is increased. Therefore, difference between different acid and alkali liquids, solvents, and air in the soil may be further analyzed, thereby setting the corresponding copper foil cross-sectional area information 331 and capacitance boundary information 332 in advance. For example, when the surface area of the copper foil 12 is 5 cm$^2$, the capacitance boundary information 332 may be set to be 20 uF, and the calculating unit 21 can analyze whether the target object contacted by the sensing unit 10 is a liquid or the sensing unit 10 contacts air. When the surface area of the copper foil 12 is 5 cm$^2$, the capacitance boundary information 332 may be set to be 360 uF, and the calculating unit 21 can analyze whether the target object contacted by the sensing unit 10 is water or an acid/alkaline solution, thereby overcoming the problem that different acidity/alkalinity of the solvent contained in the target object may influence the accuracy of water content measurement.

Furthermore, the power unit 22 may be a battery or a solar energy-to-power conversion unit. Furthermore, the battery may be a rechargeable battery and is controlled together with a solar energy-to-power conversion unit by a charging control unit. The charging control unit uses the solar energy-to-power conversion unit to charge the rechargeable battery when the battery power is exhausted. Moreover, the charging control unit may transfer power to the entire device in the charging period. However, the power supply technique is well known to persons of ordinary skill in the art, so the details will not be repeated herein again.

Referring to FIG. 1, the sensing device further includes a prompt unit 24, and the memory unit 23 stores a plurality of prompt conditions 34. When the calculating unit 21 determines that the water content of the target object meets a target prompt condition 34 among all the prompt conditions 34, the prompt unit 24 is used to output a prompt signal corresponding to the target prompt condition 34. For example, when the sensing unit 10 is configured in the soil, as the calculating unit 21 determines that the soil water content is too high, the prompt unit 24 is used to send a prompt signal that the water content is too high. As the calculating unit 21 determines that the soil water content is too low, the prompt unit 24 is used to send a prompt signal that the soil water content is too low. As the calculating unit 21 determines that the soil water content is moderate, the prompt unit 24 is used to send a prompt signal that the soil water content is moderate or takes no action. The prompt unit 24 may be a light-emitting unit, e.g., a light-emitting diode, for differentiating different prompt signals by light of different colors or different brightness. Or, the prompt unit 24 may be a sound-emitting unit, e.g., a buzzer, for differentiating different prompt signals by different long and short tones or tones with different volumes. Or, the prompt unit 24 may be a display unit, for differentiating different prompt signals by text or graphs. Or even, the prompt unit 24 may be a combination of two or more of the above types. Moreover, the prompt unit 24 may be additionally configured other than inside the sensing device.

Figure 4:
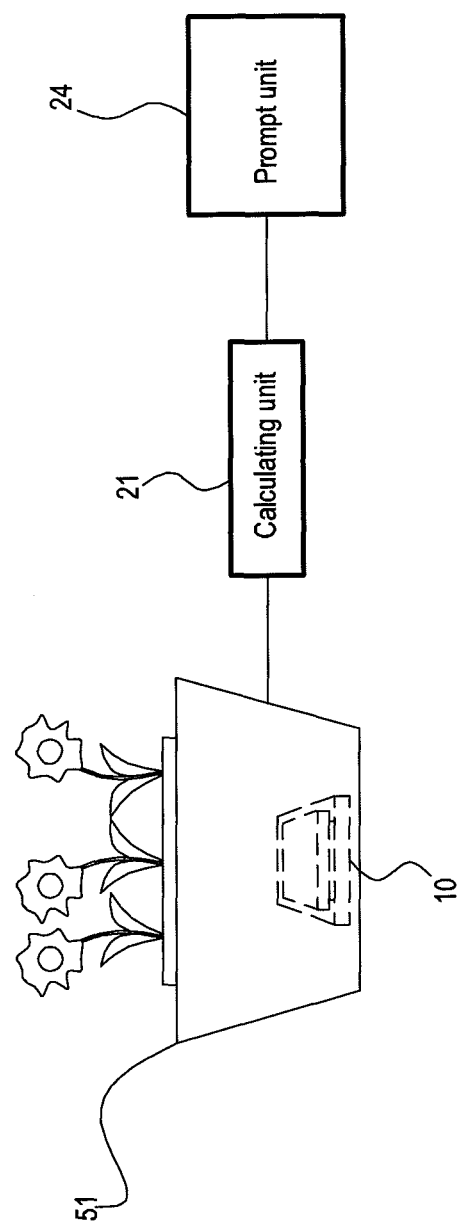
FIG. 4 illustrates a contact-type object water content sensing device according to an embodiment the present invention.

FIG. 4 illustrates a contact-type object water content sensing device according to an embodiment the present invention. Referring to FIG. 4, the sensing unit 10 is configured in the soil of a flower pot 51 and the prompt unit 24 is electrically connected to the calculating unit 21. The calculating unit 21 senses the soil water content in the flower pot 51 through the sensing unit 10, and informs the user that the soil water content is high, low, or moderate through the prompt unit 24. This configuration mode is also applicable to an electronic equipment using a liquid substance or solvent, e.g., a fridge or washing machine. The user may configure the sensing unit 10 in the electronic equipment, so the calculating unit 21 may sense the water content in the electronic equipment through the sensing unit 10, thereby the prompt unit 24 provides a relevant prompt signal.

Figure 5:
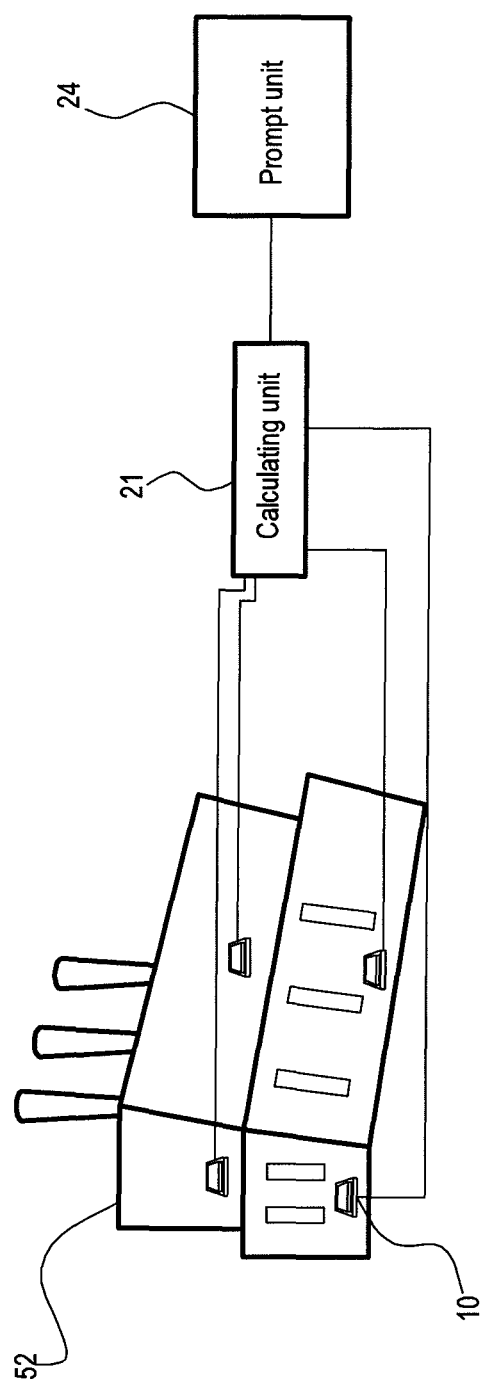
FIG. 5 illustrates a contact-type object water content sensing device according to another embodiment of the present invention.

FIG. 5 illustrates a contact-type object water content sensing device according to another embodiment of the present invention. Referring to FIG. 5, the above sensing device may be applied in a plant 52, and the user may configure a plurality of sensing units 10 in the plant 52 on the important spots where the existence of water leakage, the equipment that leaks, the production line, pipelines, and so on are put on high alert. The calculating unit 21, when sensing that the water content at any spot is abnormal through the sensing unit 10, immediately informs the management personnel by the prompt unit 24.

Figure 6:
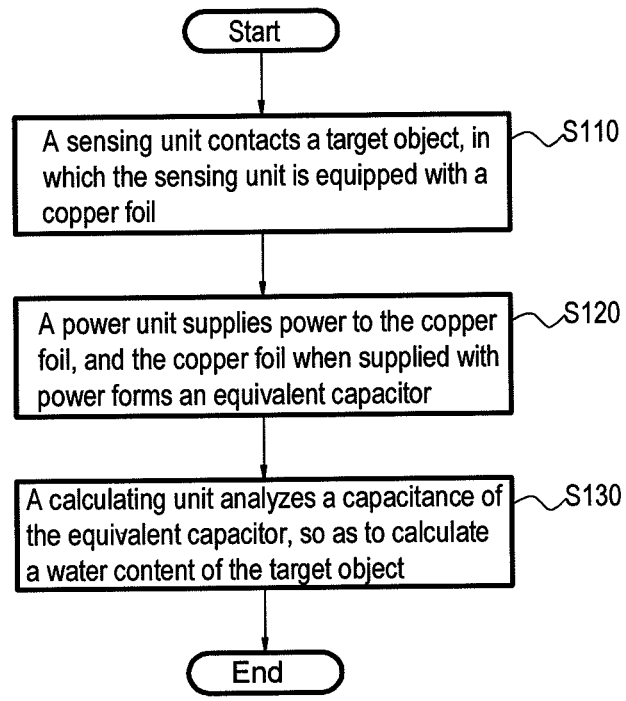
FIG. 6 is a schematic flow chart of a contact-type object water content sensing method according to an embodiment of the present invention.
Figure 7:
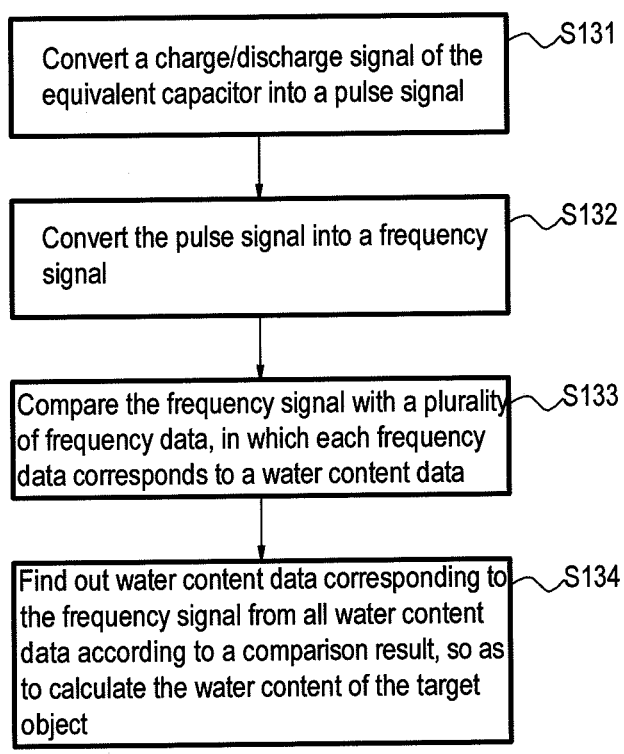
FIG. 7 is a detailed schematic flow chart of analyzing a charge/discharge signal of an equivalent capacitor to calculate a water content of a target object according to an embodiment of the present invention.
Figure 8:
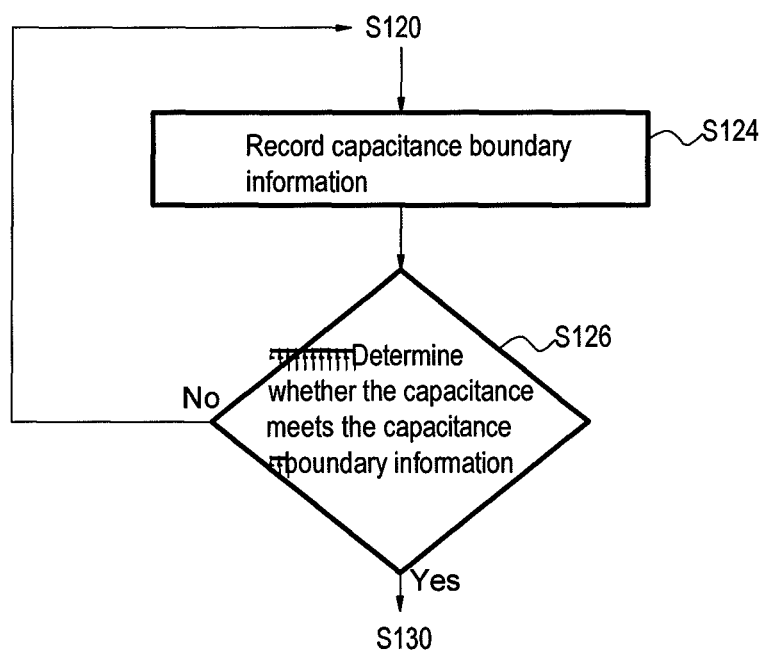
FIG. 8 is a detailed schematic flow chart of determining to start calculating the water content of the target object or not according to capacitance boundary information according to an embodiment of the present invention.

FIG. 6 is a schematic flow chart of a contact-type object water content sensing method according to an embodiment of the present invention. FIG. 7 and FIG. 8 are detailed schematic flow charts of a contact-type object water content sensing method according to an embodiment of the present invention. Referring to FIG. 6, FIG. 7, and FIG. 8 together with FIG. 1 to FIG. 3 for ease of understanding, the method is illustrated as follows.

A sensing unit 10 contacts a target object, in which the sensing unit 10 is equipped with a copper foil 12 (Step S110). As shown in FIG. 1, the sensing unit 10 includes a substrate 11 which is equipped with the copper foil 12 thereon, and a protection layer 13 may be configured on the surface of the copper foil 12.

A power unit 22 supplies power to the copper foil 12, and the copper foil 12 when supplied with power forms an equivalent capacitor (Step S120). The copper foil 12 when supplied with power and abutting the target object forms an equivalent capacitor to take a charging/discharging action.

An calculating unit 21 analyzes a capacitance of the equivalent capacitor, so as to calculate a water content of the target object (Step S130).

Furthermore, Step S130 may be divided into the following steps, as shown in FIG. 7.

A charge/discharge signal 40 of the equivalent capacitor is converted into a pulse signal 42 (Step S131). The calculating unit 21 senses the charge/discharge signal 40 of the equivalent capacitor through the copper foil 12, and when the charge/discharge signal 40 is converted into a timing diagram, a sawtooth wave is presented. The sawtooth-to-pulse wave conversion module 211 regulates the charge/discharge signal 40 to convert the sawtooth wave into the pulse signal 42.

The pulse signal 42 is converted into a frequency signal (Step S132). The pulse-to-frequency conversion module 212 calculates the frequency of the charge/discharge signal 40 to convert the pulse into the corresponding frequency signal. Depending on different signal contents of the pulse signal 42, the converted frequency signals differ.

The frequency-to-water content conversion module 213 compares the frequency signal with a plurality of frequency data 31, in which each frequency data 31 corresponds to a water content data 32 (Step S133). Thereafter, the frequency-to-water content conversion module 213 finds out water content data 32 corresponding to the frequency signal from all water content data 32 according to a comparison result, so as to calculate the water content of the target object (Step S134). However, the frequency data 31 and the water content data 32 corresponding to the frequency data 31 may be stored in the calculating unit 21 or designed in the program executed by the calculating unit 21 in advance.

Referring to FIG. 6, FIG. 8, and FIG. 1, before Step S130 is executed, the calculating unit 21 may execute the following flow in advance.

Capacitance boundary information 332 is recorded (Step S124). As described above, the memory unit 23 stores the copper foil cross-sectional area information 331 and the capacitance boundary information 332.

Thereafter, the calculating unit 21 determines whether the capacitance meets the capacitance boundary information 332 (Step S126). When it is determined that the capacitance meets the capacitance boundary information 332, the calculating unit 21 executes Step S130 to calculate the water content of the target object. Otherwise, the calculating unit 21 takes no action and returns to Step S120 to repeat Step S120 to Step S126 until the capacitance meets the capacitance boundary information 332.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A contact-type object water content sensing device, comprising:
    a sensing unit, comprising a substrate and a copper foil, wherein the copper foil is configured on the substrate, the sensing unit is used to contact a target object, and the copper foil when supplied with power forms an equivalent capacitor;
    a power unit, electrically connected to and supplying power to the copper foil;
    an calculating unit, electrically connected to the sensing unit, for analyzing a capacitance of the equivalent capacitor to calculate a water content of the target object; and
    a memory unit, for storing a plurality of frequency data and a plurality of water content data corresponding to the frequency data, wherein the calculating unit analyzes a charge/discharge signal of the equivalent capacitor, converts the charge/discharge signal into a pulse signal, and converts the pulse signal into a frequency signal, and then uses the frequency signal to compare the frequency data so as to calculate the water content of the target object according to the water content data.

2. The contact-type water content sensing device according to claim 1, wherein the sensing unit is further equipped with a protection layer, configured on a surface of the copper foil.

3. The contact-type water content sensing device according to claim 1, wherein the memory unit is electrically connected to the sensing unit, for recording capacitance boundary information, wherein the calculating unit calculates the water content of the target object when the capacitance meets the capacitance boundary information.

4. The contact-type water content sensing device according to claim 1, further comprising a prompt unit electrically connected to the sensing unit, wherein the memory unit stores a plurality of prompt conditions, and when the calculating unit determines that the water content of the target object meets a target prompt condition among the prompt conditions, the prompt unit is used to output a prompt signal corresponding to the target prompt condition.

5. A contact-type object water content sensing method, comprising:
    contacting a target object by a sensing unit, wherein the sensing unit is equipped with a copper foil;
    supplying power to the copper foil by a power unit, wherein the copper foil when supplied with power forms an equivalent capacitor; and
    analyzing a capacitance of the equivalent capacitor by a calculating unit to calculate a water content of the target object,
    wherein the step of analyzing the capacitance of the equivalent capacitor by the calculating unit to calculate the water content of the target object comprises:
    converting a charge/discharge signal of the equivalent capacitor into a pulse signal;
    converting the pulse signal into a frequency signal;

comparing the frequency signal and a plurality of frequency data, wherein each frequency data corresponds to a water content data; and finding, out water content data corresponding to the frequency signal from the water content data according to a comparison result, so a to calculate the water content of the target object.

6. The contact-type object water content sensing method according to claim 5, wherein the step of analyzing the capacitance of the equivalent capacitor by the calculating unit to calculate the water content of the target object further comprises:

recording capacitance boundary information; and determining whether the capacitance meets the capacitance boundary information to decide whether to calculate the water content of the target object.

7. A computer program product, configured in an calculating unit, wherein the calculating unit is connected to a sensing unit equipped with a copper foil, the sensing unit contacts a target object, the calculating unit reads the computer program product to execute a contact-type object water content sensing method, and the method comprises:

using a power unit to supply power to the copper foil, wherein the copper foil when supplied with power forms an equivalent capacitor according to a water content of the target object; and analyzing a capacitance of the equivalent capacitor by the calculating unit to calculate the water content of the target object, wherein the step of analyzing the capacitance of the equivalent capacitor by the calculating unit to calculate the water content of the target object comprises:

converting a charge/discharge signal of the equivalent capacitor into a pulse signal;

converting the pulse signal into a frequency signal;

comparing the frequency signal and a plurality of frequency data, wherein each frequency data corresponds to a water content data; and finding out water content data corresponding to the frequency signal from the water content data according to a comparison result, so as to calculate the water content of the target object.

* * * * *